United States Patent
Dupont-Passelaigue et al.

(10) Patent No.: US 8,993,569 B2
(45) Date of Patent: Mar. 31, 2015

(54) DIARYLPYRIDAZINONE DERIVATIVES, PREPARATION THEREOF, AND USE THEREOF FOR THE TREATMENT OF HUMANS

(75) Inventors: Elisabeth Dupont-Passelaigue, Colomiers (FR); Isabelle Le Roy, Frouzins (FR); Samuel Mialhe, Castres (FR); Christophe Pignier, Castres (FR)

(73) Assignee: Pierre Fabre Medicament, Boulogne-Billancourt (FR)

( * ) Notice: Subject to any disclaimer, the term of this patent is extended or adjusted under 35 U.S.C. 154(b) by 28 days.

(21) Appl. No.: 13/823,671

(22) PCT Filed: Dec. 20, 2011

(86) PCT No.: PCT/EP2011/073476
§ 371 (c)(1),
(2), (4) Date: Mar. 14, 2013

(87) PCT Pub. No.: WO2012/085001
PCT Pub. Date: Jun. 28, 2012

(65) Prior Publication Data
US 2013/0267520 A1 Oct. 10, 2013

(30) Foreign Application Priority Data
Dec. 22, 2010 (FR) ..................... 10 61021

(51) Int. Cl.
*A01N 43/58* (2006.01)
*A61K 31/50* (2006.01)
*C07D 237/00* (2006.01)
*C07D 237/02* (2006.01)
*C07D 237/14* (2006.01)
*C07D 231/20* (2006.01)

(52) U.S. Cl.
CPC ............ *C07D 237/14* (2013.01); *C07D 231/20* (2013.01)
USPC .......................................... 514/247; 544/239

(58) Field of Classification Search
CPC ............................ C07D 237/14; C07D 231/20
See application file for complete search history.

(56) References Cited

FOREIGN PATENT DOCUMENTS

WO       WO 98/41511 A1    9/1998
WO       WO 2006/136304 A1 12/2006

OTHER PUBLICATIONS

Dörwald, F. Zaragoza. (Side Reactions in Organic Synthesis: A Guide to Successful Synthesis Design, Weinheim: Wiley-VCH Verlag GmbH & Co. KGaA, 2005, Preface).*
Jordan, V. C. (Nature Reviews: Drug Discovery, 2, 2003, 205-213).*
Bhakta et al., "Pharmacologic Targets for Atrial Fibrillation", Expert Opinion on Therapeutic Targets, vol. 11, No. 9, Sep. 2007, pp. 1161-1178.
Blackiston et al., "Bioelectric controls of cell proliferation—Ion channels, membrane voltage and the cell cycle", Cell Cycle, vol. 8, No. 21, Nov. 1, 2009, pp. 3527-3536.
Gögelein et al., "Effects of the atrial antiarrhythmic drug AVE0118 on cardiac ion channels", Naunyn-Schmiedeberg's Arch Pharmacol, vol. 370, 2004 (published online Aug. 31, 2004), pp. 183-192.
Gutman et al., "International Union of Pharmacology. LIII. Nomenclature and Molecular Relationships of Voltage-Gated Potassium Channels", Pharmacological Reviews, vol. 57, No. 4, 2005, pp. 473-508.
International Search Report, dated Feb. 6, 2012, for International Application No. PCT/EP2011/073476.
Miyasaka et al., "Secular Trends in Incidence of Atrial Fibrillation in Olmsted County, Minnesota, 1980 to 2000, and Implications on the Projections for Future Prevalence", Circulation, Journal of the American Heart Association, vol. 114, 2006 (originally published online Jul. 3, 2006), pp. 119-125.
Nerbonne et al., "Molecular Physiology of Cardiac Repolarization", Physiol Rev., vol. 85, 2005, pp. 1205-1253.
Page et al., "Drug Therapy for Atrial Fibrillation: Where Do We Go From Here?", Nature Reviews, vol. 4, Nov. 2005, pp. 899-910.
Pardo et al., "Role of Voltage-gated Potassium Channels in Cancer", Journal of Membrane Biology, vol. 205, No. 3, Jun. 2005, pp. 115-124.
Pardo, "Voltage-Gated Potassium Channels in Cell Proliferation", Physiology, vol. 19, 2004, pp. 285-292.
Regan et al., "Atrial Antifibrillatory Effects of Structurally Distinct IKur Blockers 3-[(Dimethylamino) methyl]-6-methoxy-2-methyl-4-phenylisoquinolin-1(2H)-one and 2-Phenyl-1,1-dipyridin-3-yl-2-pyrrolidin-1-yl-ethanol in Dogs with Underlying Heart Failure", JPET, vol. 324, No. 1, 2008, pp. 322-330.
Tamargo et al., "Pharmacology of cardiac potassium channels", Cardiovascular Research, vol. 62, 2004, pp. 9-33.

* cited by examiner

*Primary Examiner* — James D Anderson
*Assistant Examiner* — William Lee
(74) *Attorney, Agent, or Firm* — Birch, Stewart, Kolasch & Birch, LLP

(57) ABSTRACT

The present invention relates to diarylpyridazinone derivatives that block the potassium Kv channels (specifically the Kv1.5, Kv4.3, and Kv11.1 channels) and to the use thereof for the treatment of humans. Said compounds have the general formula (I), where $R_1$ and $R_2$ are simultaneously or independently one or more groupings such as: halogen, such as F, Br, Cl, a straight or branched $C_1$-$C_4$ alkyl, hydroxy, a straight or branched $C_1$-$C_4$ alkoxy, arylsulfonamido, in which the aryl is optionally replaced with a straight or branched $C_1$-$C_4$ alkyl, or nitrile, as well as the various enantiomers and the mixtures thereof in any proportion, and the pharmaceutically acceptable salts thereof.

14 Claims, No Drawings

DIARYLPYRIDAZINONE DERIVATIVES, PREPARATION THEREOF, AND USE THEREOF FOR THE TREATMENT OF HUMANS

The present invention concerns diarylpyridazinone derivatives, preparation thereof and uses thereof for the treatment of humans, as blockers of the potassium Kv channels and more specifically the Kv 1.5, Kv4.3 and Kv 11.1 channels.

The potassium channels represent the largest family of ion channels in the human genome with approximately 80 genes (Tamargo et al, Cardiovasc. Res. 2004, 62: 9-33). These potassium channels may be subdivided into 3 subfamilies: potential or voltage-activated channels ($K_v$ channels) and calcium-activated channels ($K_{ca}$ channels), inwardly rectifying channels ($K_{ir}$) and 2-pore potassium channels ($K_{2p}$). The subfamily of potential-activated channels is the most widespread in the human body with virtually ubiquitous distribution in excitable cells (cardiac cells, neurones, striated or smooth muscle cells) and non-excitable cells such as pancreatic, prostatic and parathyroid cells, etc. (for review, Gutman G et al, Pharmacol. Rev. 2005, 57: 473-508).

The main function of Kv potassium channels in excitable cells is to control the resting membrane potential and the action potential duration (Nerbonne et Kass, Physiol. Rev.2005; 85:1205-1253). In this respect, several Kv channels are involved in this control, both in the cardiac auricles and ventricles. The Kv4.3 channels in conjunction with the KChIP 2 subunits form the current $I_{to}$ which is involved in the early repolarisation phase of the action potential (AP); the KVLQT1/MinK and hERG channels are involved in the late polarisation phase of the AP (respectively generating the currents $I_{Ks}$ and $I_{Kr}$). Aforesaid channels are uniformly distributed between the cardiac auricles and ventricles. Two other types of potassium channel however display a distribution solely in the auricles. The potential-dependent potassium channels ($K_{v1.5}$) responsible for the current $I_{Kur}$ and the inwardly rectifying channels activated by acetylcholine (Kir3.1 and Kir3.4 responsible for the current $I_{K-ACh}$).

Changes in membrane electrical activity are observed in many disorders, particularly cardiac disorders involving arrhythmias. Among the latter, atrial fibrillation (AF) is a serious arrhythmia involving completely desynchronised activity of the atrial myocytes resulting in uninterrupted, rapid and irregular electrical activity. AF is induced by the appearance of re-entrant electrical circuits in atrial tissue (Miyasaka Y et al, Circulation 2006, 114: 119-125). No specific antiarrhythmic treatment of the atrial level currently exists in order to reduce the incidence of AF, which therefore represents a major medical necessity (Page et Roden, Nat. Rev. Drug Discov. 2005, 4: 899-910).

The presence of a large number of simultaneously activated micro-re-entrant circuits explains the anarchic nature of the electrical activity observed both via the endocavitary route and on the ECG. This arrhythmia generally develops against a background of an atrial myocardium which is pathological from the electrophysiological point of view, the refractory periods of which are too short and highly uneven in relation to one another and hence highly vulnerable to the slightest extrasystole. These abnormalities fall within the context of a phenomenon of myocardial remodelling, following pressure overload or stretching causing morphological changes (hypertrophy, dilation, fibrosis) in addition to modifications in transmembrane ionic current regulation, modifying the electrophysiological characteristics of the atrial myocytes. Given that each bout of AF maintains or even worsens this process of mechanical and electrophysiological remodelling, it is understandable that AF has a high potential for recurrence and its natural evolution is towards chronicity. Conversely, instances of AF of the focal type have recently been identified, originating at a specific point which is almost always observed to be an extension of the atrial myocardium into the pulmonary veins. These fairly rare cases of AF adopt a fairly monomorphic character, at any rate comparable to the atrial extrasystoles at the outset of the bout or intermittently observed between the attacks. In all cases, loss of the atrial systole results in a reduction in cardiac output varying between 20 and 30% and all the more pronounced in that the latter is diminished in the basal state. In parallel, existence of blood stasis in the atrial cavities, particularly in some culs-de-sac such as the auricles, accounts for the thromboembolitic risk. However, the risk of embolism is only partly influenced by the mere presence of AF, with the atrial stasis also being related to the increase in the intracavitary pressures (systolic or diastolic left ventricular dysfunction, valvulopathy or prosthetic valve).

Electrical remodelling therefore constitutes the major substrate of the genesis of AF; it is the result of a reduction in the activity of the L-type calcium channels, allowing the Kv1.5 potassium channels to fully exercise their repolarising role by means of the ultra-rapid potassium current (Bhakta et Miller, Expert Opin. Ther. Targets 2007, 11: 1161-1178). The result is a dramatic reduction in the refractory period which represents the precipitating factor for the micro-re-entries. With the knowledge that the Kv1.5 potassium channels are not functionally expressed at the ventricular level, a blocker of these channels will therefore represent a selective antiarrhythmic of the atrial level without affecting ventricular electrophysiology. Its pharmacological effect manifests itself in an extension of the refractory period and therefore less effect of the micro-re-entrant circuits. A number of experimental data obtained with reference products confirm the value of Kv1.5 blocking as a therapeutic target (Gogelein et al, Naunyn Schmiedeberg's Arch Pharmacol 2004, 370: 183-192, Regan et al, J Pharmacol Exp Ther 2008, 324: 322-330).

The rapid changes in the membrane potential are well known in excitable cells, but slow variations in potential are observed in all cells and are associated with control of the cell cycle. The cell cycle is a key parameter in cell behaviour which needs to be regulated and coordinated for development, tissue regeneration and cell proliferation (Pardo, Physiology, 2004; 19:285-292; Blackistion et al, Cell Cylce, 2009; 8-21: 3527-3536). Generally speaking, blocking of the potassium channels leads to a decrease in proliferation in physiological models (such as in lymphocytes) and pathological models (cancer). The role of the potassium channels in regulating the cell cycle was demonstrated in many cell types, whether physiological or pathological (cancerous lines or tumours) derived from human melanoma, lung cancer, lymphoma, mesothelioma, hepatocarcinoma, lymphocytes and monocytes (for review Pardo et al, J. Membr. Biol, 2005; 205: 115-124).

As used above, the term "Kv" indicates the potential-dependent family of potassium channels and comprises different subfamilies (Kv1., Kv2., Kv3 . . . ) among which the Kv1.1, Kv1.2 and Kv1.3 . . . channels are to be found.

"A Kv channel blocker" denotes a molecule that reduces or blocks the $K^+$ ion flow through the channel.

As used herein, the term "salts" refers to the inorganic acid and base addition salts of the compounds of the present invention. The salts are preferably pharmaceutically acceptable, i.e. they are non-toxic to the patient to whom they are administered. The term "pharmaceutically acceptable" refers to molecular entities and compositions which do not result in any adverse or allergic effect or any other undesirable reaction when administered to an animal or human. When used herein, the term" pharmaceutically acceptable excipient" includes any diluent, adjuvant or excipient, such as preservative agents, filling agents, disintegrating, wetting, emulsifying, dispersing, antibacterial or antifungal agents, or furthermore agents allowing delay of absorption or intestinal and digestive resorption. Use of these media or vectors is well known to the art. Unless the agent is chemically incompatible with a diarylpyridazinone derivative, its use in pharmaceutical compositions with the compounds according to the invention is envisaged. Within the context of the invention, the term "treatment" as used herein means preventing or inhibiting occurrence or progression of the disorder to which the term applies or indeed one or several symptoms of this disorder.

The subject of the present invention is diarylpyridazinone derivatives that block the potassium Kv channels (more specifically the Kv 1.5, Kv4.3 and Kv 11.1 channels) and use thereof for the treatment of humans.

These compounds correspond to the general formula

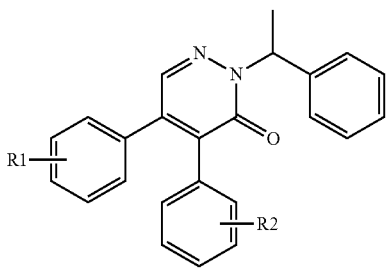

wherein $R_1$ and $R_2$ simultaneously or independently represent one or several groups chosen from: halogen such as F, Br, Cl, linear or branched C1-C4 alkyl, hydroxy, linear or branched $C_1$-$C_4$ alkoxy, nitrile or arylsulfonamido the aryl of which is optionally substituted by a linear or branched $C_1$-$C_4$ alkyl group, as well as the different enantiomers and their mixtures in all proportions, and their pharmaceutically acceptable salts.

Within the context of the present invention, the aryl group designates hydrocarbonated aromatic 5- or 6-membered monocycles.

According to an embodiment of the invention, the compounds of general formula I are those for which:

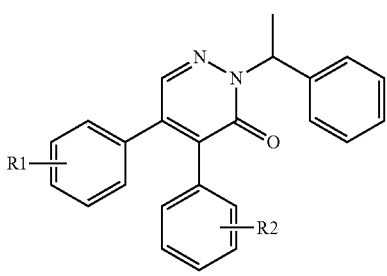

$R_1$ represents a hydroxy, methoxy or cyano group; $R_2$ represents several groups chosen from: halogen such as F, Br, Cl, linear or branched $C_1$-$C_4$ alkyl, hydroxy, linear or branched $C_1$-$C_4$ alkoxy, nitrile; as well as the different enantiomers and their mixtures in all proportions, and their pharmaceutically acceptable salts.

According to another embodiment of the invention, the compounds of general formula I are those for which:

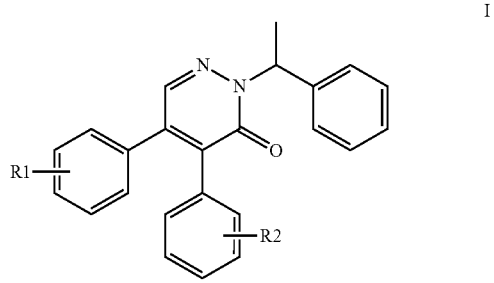

$R_1$ represents a hydroxy group,
$R_2$ represents several groups chosen from: halogen such as F, Cl, linear or branched $C_1$-$C_4$ alkyl, hydroxy, linear or branched $C_1$-$C_4$ alkoxy, nitrile; as well as the different enantiomers and their mixtures in all proportions, and their pharmaceutically acceptable salts.

According to another embodiment of the invention, the compounds of general formula I are those for which:

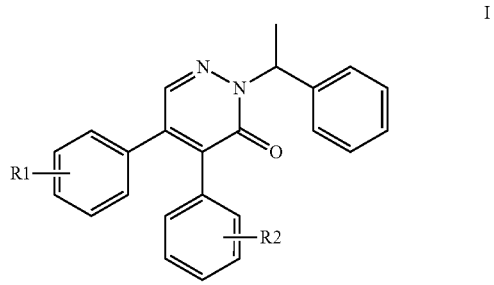

$R_1$ represents a hydroxy group located in para position (position 4) on the phenyl which it substitutes, $R_2$ represents several groups chosen from: Cl, methyl, hydroxy, methoxy, nitrile; as well as the different enantiomers and their mixtures in all proportions, and their pharmaceutically acceptable salts.

The present invention concerns the compounds of general formula I, characterised in that they are chosen from:
1. 4,5-Bis-(4-hydroxy-phenyl)-2-(1-phenyl-ethyl)-2H-pyridazin-3-one
2. 4,5-Bis-(4-hydroxy-phenyl)-2-((S)-1-phenyl-ethyl)-2H-pyridazin-3-one
3. 4,5-Bis-(4-hydroxy-phenyl)-2-((R)-1-phenyl-ethyl)-2H-pyridazin-3-one
4. 2,2'-(6-oxo-1-(1-phenyl-ethyl)-1,6-dihydropyridazine-4,5-diyl) dibenzonitrile
5. 3,3'-(6-oxo-1-(1-phenyl-ethyl)-1,6-dihydropyridazine-4,5-diyl) dibenzonitrile
6. 4,5-Bis-(4-methoxy-phenyl)-2-(1-phenyl-ethyl)-2H-pyridazin-3-one
7. N,N'-(3,3'-(6-oxo-1-(1-phenyl-ethyl)-1,6-dihydropyridazine-4,5-diyl) bis(3, 1- phenylene))bis(4-methylbenzenesulfonamide)
8. 3-(5-(4-methoxy-phenyl)-6-oxo-1-(1-phenylethyl)-1,6-dihydropyridazin-4-yl) benzonitrile 9. 2-[5-(4-Methoxy-phenyl)-6-oxo-1-(1-phenyl-ethyl)-1,6-dihydro-pyridazin-4-yl]-benzonitrile 10. N-{3-[5-(3,4-Dimethyl-phenyl)-6-oxo-1-(1-phenyl-ethyl)-1,6-dihydropyridazin-4-yl]-phenyl}-4-methyl-benzenesulfonamide 11. 4,5-Bis-(3,4-dichloro-phenyl)-2-(1-phenyl-ethyl)-2H-pyridazin-3-one The present invention also covers the different enantiomers of the compounds of general formula I, as well as their mixtures in all proportions.

The mixtures of the enantiomers in all proportions also include racemic mixtures.

The subject-matter of the invention likewise concerns the different enantiomers and their mixtures in all proportions of the compounds of general formula I as well as the pharmaceutically acceptable salts.

The present invention also covers the processes for chemical preparation of the compounds of general formula I as well as the different enantiomers and their mixtures in all proportions.

The two enantiomers may be prepared enantioselectively from the (R)- or (S)-1-phenylethanols respectively. Furthermore, based on the racemic, it is possible to obtain both enantiomers by preparative HPLC separation on a chiral column (for example Chiralpack AD-H, eluent: heptane/EtOH/diethylamine).

The present invention likewise concerns the compounds of general formula I as well as different enantiomers and their mixtures in all proportions and their pharmaceutically acceptable salts for use thereof as blockers of the potassium Kv channels and more specifically the Kv 1.5, Kv4.3 and Kv 11.1 channels.

The present invention likewise concerns the compounds of general formula I as well as the different enantiomers and their mixtures in all proportions and the pharmaceutically acceptable salts thereof for use thereof as a medicament.

The invention also concerns the compounds of general formula I as well as different enantiomers and their mixtures in all proportions and their pharmaceutically acceptable salts for use thereof as a medicament intended for treatment and/or prevention of diseases requiring blockers of potassium Kv channels and more specifically the Kv 1.5, Kv4.3 and Kv 11.1 channels.

The invention also concerns the compounds of general formula I as well as the different enantiomers and their mixtures in all proportions and the pharmaceutically acceptable salts thereof for their use as a medicine intended for treatment and/or prevention of diseases such as atrial fibrillation and auricular and/or ventricular cardiac arrhythmias, but also diseases in which the cell cycle, cell proliferation and regeneration are modified (cancer, chronic inflammation).

The invention also covers the compositions characterised in that they contain as the active substance a compound of general formula I or one of the enantiomers thereof and their mixtures in all proportions, or one of the pharmaceutically acceptable salts thereof.

The invention also concerns a pharmaceutical composition characterised in that it contains a compound of general formula I or one of the enantiomers thereof and their mixtures in all proportions or one of the pharmaceutically acceptable salts thereof in combination with any pharmaceutically acceptable excipient.

The pharmaceutical compositions according to the invention may be administered via the oral, sublingual, subcutaneous, intramuscular, intravenous, transdermal, local or rectal route. In this case, the active substance may be administered in unit forms of administration, in a mixture with conventional pharmaceutical carrier, to animals or humans. Appropriate unit forms of administration comprise forms via the oral route such as tablets, capsules, powders, granules and oral solutions or suspensions, sublingual and buccal forms of administration, subcutaneous, topical, intramuscular, intravenous, intranasal or intraocular forms of administration and rectal forms of administration. The appropriate formulations for the chosen form of administration are known to the person skilled in the art and are described for example in: Remington, The science and Practice of Pharmacy, 19th edition, 1995, Mack Publishing Company.

The dosages of the compounds of formula I in the compositions of the invention may be adjusted in order to obtain a quantity of active substance that is effective in order to obtain the desired therapeutic response for a composition specific to the method of administration. The effective dose of a compound according to the invention varies depending on a large number of parameters such as for example the selected route of administration, weight, age, sex and nature of the disease in addition to the sensitivity of the person to be treated. Consequently, the optimum dosage needs to be determined by the specialist in the subject as a function of the parameters deemed relevant.

Synthesis

The compounds of the present invention may be synthesised using the synthetic routes described below or by using synthetic methods known to the person skilled in the art.

This method of synthesis of the compounds of general formula I (FIG. 1) is characterised in that a dibromo or dichloro pyridazinone of general formula II is condensed for which X represents either a chlorine atom or a bromine atom,

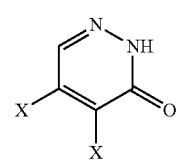

II with a derivative of general formula III,

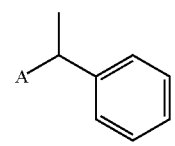

III for which
  when A represents a halogen atom such as a chlorine or a bromine atom, a base such as $Cs_2CO_3$ is used in a solvent such as dimethylformamide.
  when A represents OH, Mitsunobu coupling conditions are used such as in presence of ethyl diethylazodicarboxylate and triphenylphosphine in a solvent such as THF. These conditions are in particular applicable to enantioselective synthesis of compounds of general formula I from the (R) or (S)-1-phenylethanol.

The intermediate IV obtained

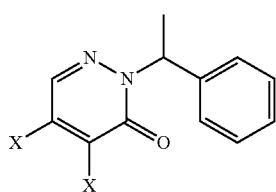

is then coupled (step 1) with a boron derivative

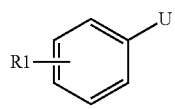

for which R1 is as defined in the general formula I and U represents

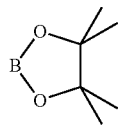

in a mixture of solvents such as toluene/ethanol or water/acetonitrile or dioxane/water in the presence of a base such as sodium or potassium carbonate and a catalyst such as tetrakis (triphenylphosphine)palladium or $PdCl_2/2PPh_3$.

These operating conditions mainly lead to formation of compound VI and minimally result in formation of compound VII.

The intermediate VI is then reacted again (step 2):
either with the boron derivative V under the coupling conditions described above, yielding compound VII.
or with the boron derivative VIII

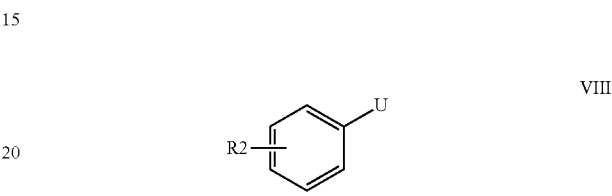

for which $R_2$ is as defined in the general formula I and U is as defined above in the coupling conditions previously described for step 1 in order to yield the compound IX.

FIG. 1

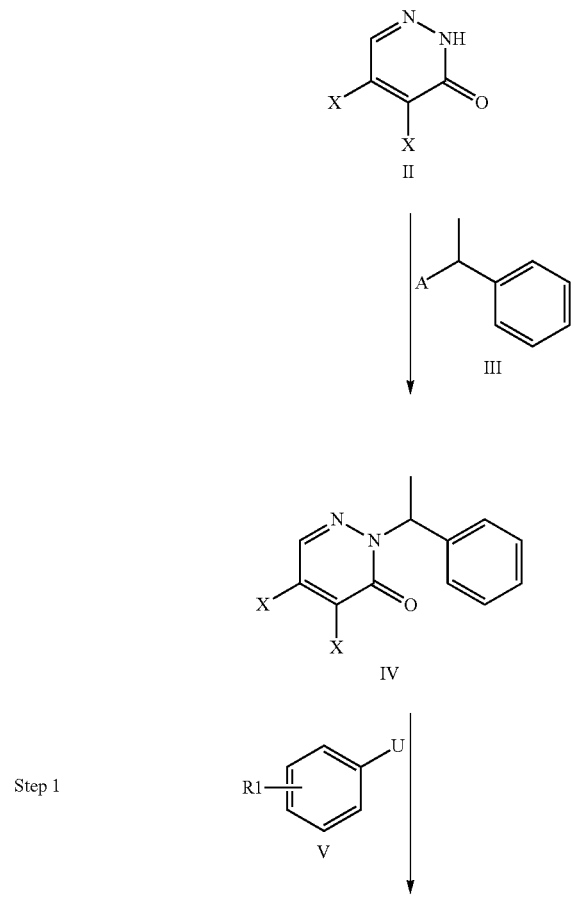

-continued

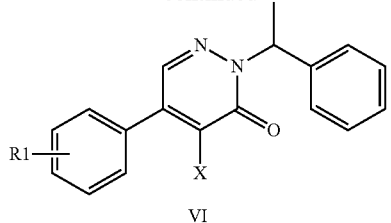

VI

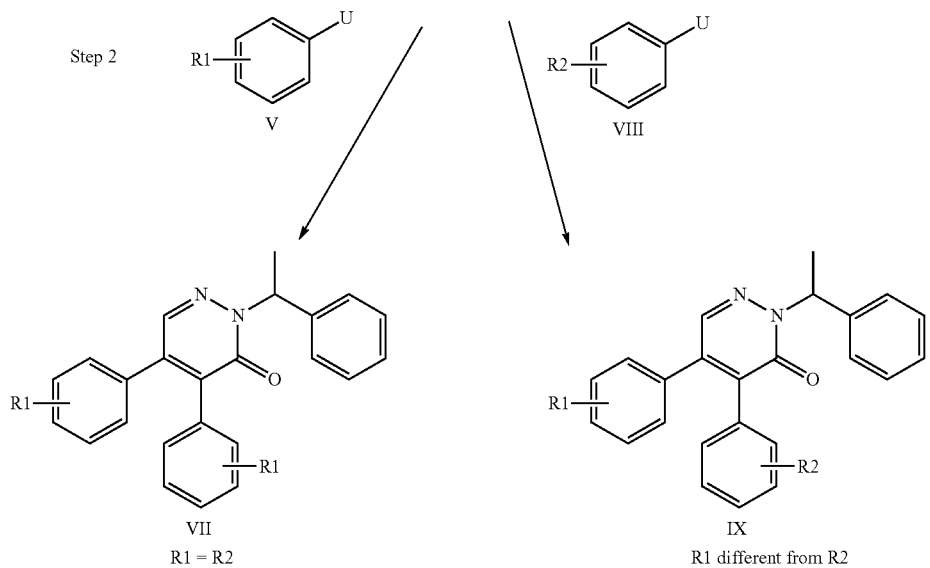

The intermediate and final compounds may, if desired, be purified according to one or several purification methods chosen from extraction, filtration, chromatography on silica gel, normal phase or reverse phase or chiral preparative HPLC and crystallisation.

The starting materials used in the processes described above are commercially available or are readily accessible to the person skilled in the art according to processes described in the literature.

The following examples illustrate the invention without limiting the scope thereof.

The elemental analyses and the mass and NMR spectra confirm the structures of the compounds.

EXAMPLES

A) Intermediates
Intermediates 1:

a) 4,5-dichloro-2-(1-phenylethyl)pyridazin-3(2H)-one (1a)

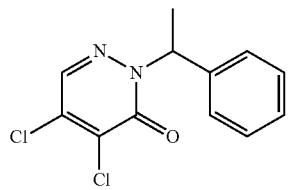 [SMILES: CC(c1ccccc1)n1ncc(Cl)c(Cl)c1=O]

The 4,5-dichloropyridazin-3(2H)-one (20 g, 121 mmol) is placed in presence of 1-bromoethyl)benzene (33.7 g, 182 mmol) and cesium carbonate (47.4 g, 145 mmol) in 100 mL of DMF at ambient temperature for 4 h. Following concentration to dryness, the residue is taken up with water and is extracted using ethyl acetate. The organic layers are dried and subsequently concentrated to dryness. The residue obtained is purified by flash chromatography on silica (Petroleum ether-AcOEt: 95-5). 31g of clear oil is obtained (yield 95%). TLC silica gel 60 F 254 Merck, Petroleum ether-AcOEt: 90-10, Rf=0.50.

b) 4,5-Dichloro-2-((S)-1-phenyl-ethyl)-2H-pyridazin-3-one (1b)

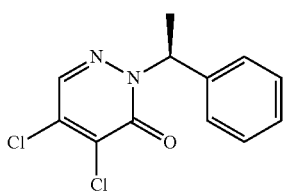 [SMILES: C[C@@H](c1ccccc1)n1ncc(Cl)c(Cl)c1=O]

The 4,5-dichloropyridazin-3(2H)-one (1.35 g, 8.2 mmol) is placed in 30 mL of THF in the presence of (R)-1-phenylethanol (1 g, 8.2 mmol) and triphenylphosphine (2.15 g, 8.2 mmol) to which ethyl diethylazodicarboxylate is added (1.71 g, 9.82 mmol. The reaction medium is stirred overnight at ambient temperature and subsequently concentrated to dryness. The residue is taken up with water and is extracted with dichloromethane on an SPE column (diatomaceous earth). The organic layers are concentrated to dryness and the residue obtained is purified by flash chromatography on silica (CH$_2$Cl$_2$). 2.1 g of yellow oil is isolated (yield 80%). TLC silica gel 60 F 254 Merck, CH$_2$Cl$_2$-MeOH:95-5, Rf=0. 66.

c) 4,5-Dichloro-2-((R)-1-phenyl-ethyl)-2H-pyridazin-3-one (1c)

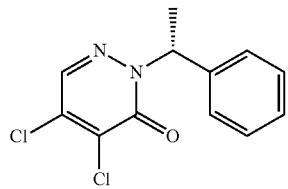

The intermediate 1 c (oil) is prepared from (S)-1-phenylethanol according to the operating method described for the intermediate lb (77%). TLC silica gel 60 F 5 254 Merck, CH$_2$Cl$_2$-MeOH:90-10, Rf=0.82.

B) Compounds According to the Invention

Example 1

4,5-Bis-(4-hydroxy-phenyl)-2-(1-phenyl-ethyl)-2H-pyridazin-3-one (1)

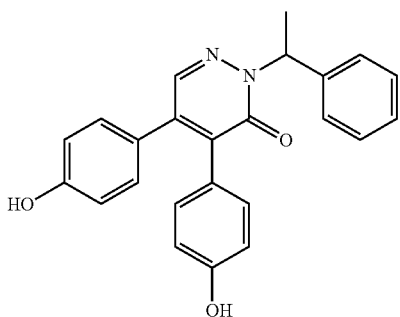 [SMILES: CC(c1ccccc1)n1ncc(-c2ccc(O)cc2)c(-c2ccc(O)cc2)c1=O]

The compound 1 is prepared according to the following method of synthesis:

Step 1: the intermediate 1a (8.7 g, 32.3 mmol) is placed in presence of tetrakis(triphenylphosphine)palladium(0) (1.12 g, 0.97 mmol) and sodium carbonate (6.85 g, 64.7 mmol) in a mixture of 50 mL of toluene and 50 mL of ethanol and the mixture is heated to 80° C. 1.2 equivalent of 4-hydroxyphenylboronic acid is added and the mixture is heated under reflux for 5 h and 1.2 additional equivalent of 4-hydroxyphenylboronic acid is added and the reflux is maintained throughout the night. Following concentration to dryness, the residue is taken up with water and is extracted using AcOEt. After drying the organic layers and concentration to dryness, the residue obtained is purified by flash chromatography (CH$_2$Cl$_2$-MeOH, gradient 100-0 to 97-3 over 40 min.). 0.7g of minority compound 1 is obtained and 8.2g of solid corresponding to the majority substituted mono product 4-chloro-5-(4-hydroxyphenyl)-2-(1-phenylethyl)-pyridazin-3(2H)-one is obtained (yield:78%).

Step 2: this substituted mono product is reacted again under the conditions described for step 1 (2.4 equivalents of 4-hydroxyphenylboronic acid, reflux overnight). Following treatment of the reaction medium, the residue obtained is purified by flash chromatography (CH$_2$Cl$_2$-MeOH, gradient 100-0 to 98-2 over 20 min.). The residue is triturated in a mixture of diethylether-CH$_2$Cl$_2$-MeOH: 40-5-2 and the compound 1 (solid) obtained is isolated by filtration (7.2g, yield 78%).

TLC silica gel 60 F 254 Merck, CH$_2$Cl$_2$-MeOH: 95-5, Rf=0.35. F=160° C.

NMR $^1$H (DMSO-d6) ppm: 9.56 (m, 2H), 8.02 (s, 1H), 7.39 (m, 5H), 6.96 (m, 4H), 6.63 (m, 4H), 6.24 (m,1 H), 1.72 (d, 3H).

MS (+ESI) m/z 385 (MH+)

Example 2

4,5-Bis-(4-hydroxy-phenyl)-2-((S)-1-phenyl-ethyl)-2H-pyridazin-3-one (2)

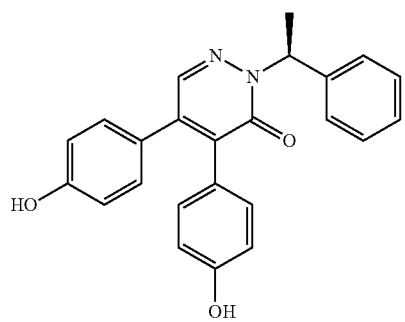 [SMILES: C[C@@H](c1ccccc1)n1ncc(-c2ccc(O)cc2)c(-c2ccc(O)cc2)c1=O]

Compound 2 is prepared according to the method of synthesis described for example 1 from the intermediate 1c (yield: 85%).

TLC silica gel 60 F 254 Merck, CH$_2$Cl$_2$-MeOH: 90-10, Rf=0.60.

F=168° C.

NMR $^1$H (DMSO-d6) ppm: 9.70 (s, 1H), 9.54 (s, 1H), 8.02 (s, 1H), 7.39 (m, 5H), 6.97 (m, 4H), 6.63 (m, 4H), 6.24 (m,1 H), 1.72 (d, 3H).

MS (+ESI) m/z 385 (MH+)

$\alpha_{calc}$ (MeOH)=−256.5°

Chiral HPLC: Chiralpack column AD-H 250*4.6 mm DAI, eluent (1 mL/min.): heptane/EtOH/diethylamine: 80/20/0.1, retention time: 8.92 min.

Example 3

4,5-Bis-(4-hydroxy-phenyl)-2-((R)-1-phenyl-ethyl)-2H-pyridazin-3-one (3)

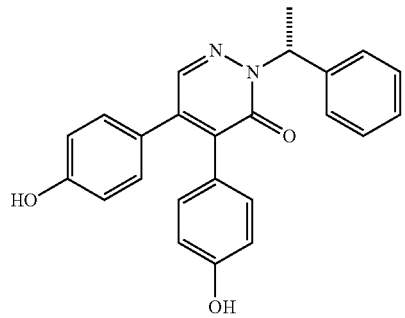 [SMILES: C[C@H](c1ccccc1)n1ncc(-c2ccc(O)cc2)c(-c2ccc(O)cc2)c1=O]

Compound 3 is prepared according to the method of synthesis described for example 1 from the intermediate 1b (yield: 43%).

TLC silica gel 60 F 254 Merck, CH$_2$Cl$_2$-MeOH: 90-10, Rf=0.60.

F=222° C.

NMR $^1$H (DMSO-d6) ppm: 9.70 (s, 1H), 9.54 (s, 1H), 8.02 (s, 1H), 7.39 (m, 5H), 6.97 (m, 4H), 6.63 (m, 4H), 6.24 (m,1 H), 1.72 (d, 3H).

MS (+ESI) m/z 385 (MH+)

α$_{calc}$ (MeOH)=272.2°

Chiral HPLC: Chiralpack column AD-H 250*4.6 mm DAI, eluent (1 mL/min.): heptane/EtOH/diethylamine: 80/20/0.1, retention time: 7.23 min.

Example 4

2,2'-(6-oxo-1-(1-phenylethyl)-1,6-dihydropyridazine-4,5-diyl)dibenzonitrile (4)

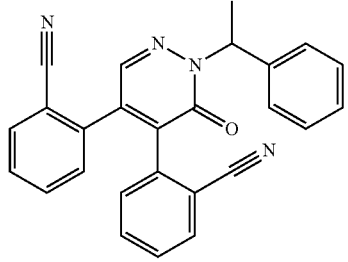 [SMILES: CC(c1ccccc1)n1ncc(-c2ccccc2C#N)c(-c2ccccc2C#N)c1=O]

Compound 4 is prepared from the intermediate 1a and 2-(4,4,5,5-tetramethyl-1,3,2-dioxaborolan-2-yl)benzonitrile according to step 1 of the method of synthesis using PdCl$_2$/2PPh$_3$, Na$_2$CO$_3$ and a mixture of water/acetonitrile: 1/1. The minor product formed corresponds to compound 4 (yield: 3.4%).

TLC silica gel 60 F 254 Merck, CH$_2$Cl$_2$, Rf=0.23.

F=200° C.

NMR $^1$H (DMSO-d6) ppm: 8,19 (s, 1H), 7.80 (d, 2H), 7.75 (d, 2H), 7.36 (m, 9H), 6.27 (q, 1H), 1.76 (d, 3H).

MS (+ESI) m/z 403 (MH+)

Example 5

3,3'-(6-oxo-1-(1-phenylethyl)-1,6-dihydropyridazine-4,5-diyl) dibenzonitrile (5)

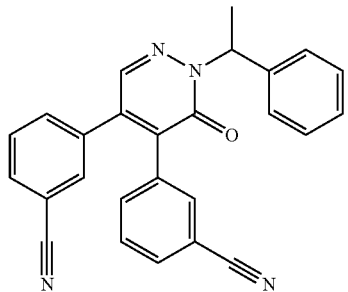 [SMILES: CC(c1ccccc1)n1ncc(-c2cccc(C#N)c2)c(-c2cccc(C#N)c2)c1=O]

Compound 5 is prepared from intermediate 1a and 3-cyanophenylboronic acid under the conditions described for example 4. The minor product formed (solid) corresponds to compound 4 (yield:7.4%).

TLC silica gel 60 F 254 Merck, CH$_2$Cl$_2$, Rf=0.11.

F=202° C.

NMR $^1$H (DMSO-d6) ppm: 8.23 (s, 1H), 7.78 (m, 3H), 7.72 (s, 1H), 7.40 (m, 9H), 6.28 (q, 1H), 1.77 (d, 3H).

MS (+ESI) m/z 403 (MH+)

Example 6

4,5-Bis-(4-methoxy-phenyl)-2-(1-phenyl-ethyl)-2H-pyridazin-3-one (6)

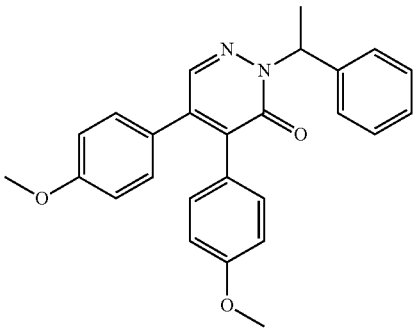 [SMILES: COc1ccc(-c2cnn(C(C)c3ccccc3)c(=O)c2-c2ccc(OC)cc2)cc1]

Compound 6 is prepared from intermediate 1a and 4-methoxyphenylboronic acid under the conditions described for example 1 using tetrakis(triphenylphosphine)palladium(0), K$_2$CO$_3$ and a mixture of dioxane/water: 3/1. Compound 6 is isolated in solid form (yield: 71%).

TLC silica gel 60 F 254 Merck, Petroleum ether-AcOEt: 80-20, Rf=0.20.

NMR $^1$H (CDCl$_3$) ppm: 7.88 (s, 1H), 7.53 (d, 2H), 7.37-7.31 (m, 2H), 7.30-7.26 (m, 1H), 7.14-7.13 (d, 2H), 7.06-7.02 (d, 2H), 6.80-6.75 (m, 4H), 6.47-6.40 (m, 1H), 3.78 (s, 3H), 3.77 (s, 3H), 1.83 (s, 3H).

MS (+ESI) m/z 413 (MH+)

Example 7

N,N'-(3,3'-(6-oxo-1-(1-phenylethyl)-1,6-dihydropyridazine-4,5-diyl)bis(3,1-phenylene))bis(4-methyl-benzenesulfonamide) (7)

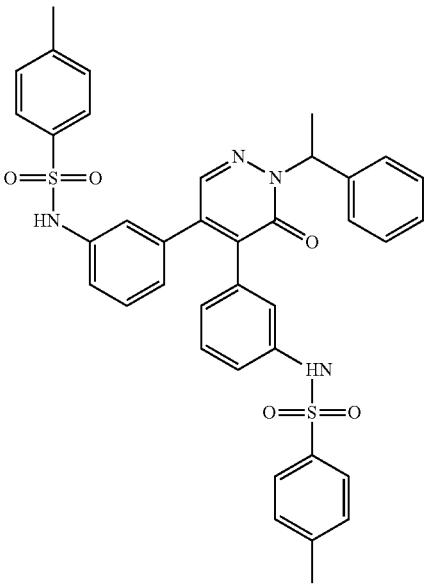 [SMILES: Cc1ccc(S(=O)(=O)Nc2cccc(-c3cnn(C(C)c4ccccc4)c(=O)c3-c3cccc(NS(=O)(=O)c4ccc(C)cc4)c3)c2)cc1]

Compound 7 is prepared from intermediate 1a and 4-methyl-N-(3-(4,4,5,5-tetramethyl-1,3,2-dioxaborolan-2-yl) phenyl) benzenesulfonamide under the conditions described for example 6. Compound 7 is isolated in solid form (yield: 74%).

TLC silica gel 60 F 254 Merck, Petroleum ether-AcOEt: 50-50, Rf=0.46.

F=202° C.

NMR ¹H (DMSO) ppm: 10.26 (s, 1H), 10.14 (s, 1H), 7.92 (s, 1H), 7.53 (d, 4H), 7.42-7.25 (m, 9H), 7.08-6.88 (m, 6H), 6.52 (dd, 2H), 6.26-6.18 (m, 1H), 2.31 (s, 6H), 1.74 (d, 3H).
MS (+ESI) m/z 691 (MH+)

Example 8

3-(5-(4-methoxyphenyl)-6-oxo-1-(1-phenylethyl)-1,6-dihydropyridazin-4-yl)benzonitrile

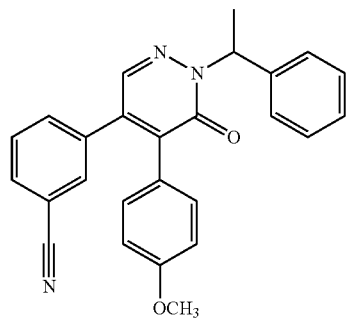 [SMILES: COc1ccc(-c2c(-c3cccc(C#N)c3)cnn(C(C)c3ccccc3)c2=O)cc1]

Compound 8 is prepared from intermediate 1a and 3-cyanophenylboronic acid according to step 1 of the method of synthesis using PdCl₂/2PPh₃, Na₂CO₃ and a mixture of water/acetonitrile: 1/1. The major product formed (1.96 g, 3-(5-chloro-6-oxo-1-(1-phenylethyl)-1,6-dihydropyridazin-4-yl)benzonitrile, yield: 19%) is isolated and subsequently introduced into step 2 of the method of synthesis using 4-methoxyphenylboronic acid with tetrakis(triphenylphosphine)palladium(0), K₂CO₃ and a mixture of dioxane/water: 2/1. Compound 8 is isolated in solid form (yield: 62%).
TLC silica gel 60 F 254 Merck, Petroleum ether-AcOEt: 50-50, Rf=0.53.
F=198° C.
TLC silica gel 60 F 254 Merck, Petroleum ether-AcOEt: 50-50, Rf=0.53.
NMR ¹H (DMSO-d6) ppm: 8.13 (s, 1H), 7.77 (m, 2H), 7.38 (m, 7H), 7.09 (d, 2H), 6.81 (d, 2H), 6.28 (q, 1H), 3.71 (s, 3H), 1.75 (d, 3H).
MS (+ESI) m/z 408 (MH+)

Example 9

2-[5-(4-Methoxy-phenyl)-6-oxo-1-(1-phenyl-ethyl)-1,6-dihydro-pyridazin-4-yl]-benzonitrile

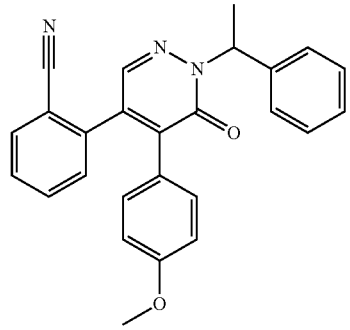 [SMILES: COc1ccc(-c2c(-c3ccccc3C#N)cnn(C(C)c3ccccc3)c2=O)cc1]

Compound 9 is prepared from intermediate 1a and 2-(4,4,5,5-tetramethyl-1,3,2-dioxaborolan-2-yl)benzonitrile according to step 1 of the method of synthesis using PdCl₂/2PPh₃, Na₂CO₃ and a mixture of water/acetonitrile: 1/1. The major product formed (1.5 g, 2-(5-chloro-6-oxo-1-(1-phenylethyl)-1,6-dihydropyridazin-4-yl) benzonitrile, yield: 16%) is isolated and subsequently introduced into step 2 of the method of synthesis with 4-methoxyphenylboronic acid using tetrakis(triphenylphosphine)palladium(0), K₂CO₃ and a mixture of dioxane/water: 2/1. Compound 9 is isolated in solid form (yield: 71%).
TLC silica gel 60 F 254 Merck, Petroleum ether-AcOEt: 70-30, Rf=0.45.
F=176°C
TLC silica gel 60 F 254 Merck, Petroleum ether-AcOEt: 50-50, Rf=0.53.
NMR ¹H (DMSO-d6) ppm: 8.09 (s, 1H), 7.79 (d, 2H), 7.40 (m, 7H), 7.08 (d, 2H), 6.81 (d, 2H), 6.28 (q, 1H), 3.71 (s, 3H), 1.75 (d, 3H).
MS (+ESI) m/z 408 (MH+)

Example 10

N-{3-[5-(3,4-Dimethyl-phenyl)-6-oxo-1-(1-phenyl-ethyl)-1,6-dihydro-pyridazin-4-yl]-phenyl}-4-methyl-benzenesulfonamide (10)

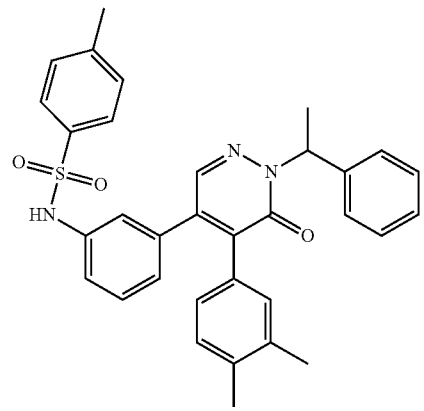 [SMILES: Cc1ccc(S(=O)(=O)Nc2cccc(-c3cnn(C(C)c4ccccc4)c(=O)c3-c3ccc(C)c(C)c3)c2)cc1]

Compound 10 is prepared from intermediate 1a and 4-methyl-N-(4-(4,4,5,5-tetramethyl-1,3,2-dioxaborolan-2-yl) phenyl)benzenesulfonamide according to step 1 of the method of synthesis using PdCl₂/2PPh₃, Na₂CO₃ and a mixture of water/acetonitrile: 1/1. The major product formed (-N-(3-(5-chloro-6-oxo-1-(5g, 1-phenylethyl)-1,6-dihydropyridazin-4-yl)phenyl)-4-methylbenzenesulfonamide, yield: 62%) is isolated and subsequently introduced into step 2 of the method of synthesis with 3,4-dimethylphenylboronic acid using tetrakis(triphenylphosphine)palladium(0), K₂CO₃ and a mixture of dioxane/water: 2/1. Compound 10 is isolated in solid form (yield: 67%).
TLC silica gel 60 F 254 Merck, CH₂Cl₂-MeOH: 97.5-2.5, Rf=0.65.
NMR ¹H (DMSO) ppm: 10.24 (s, 1H), 7.92 (s, 1H), 7.54 (d, 2H), 7.41-7.26 (m, 7H), 7,10 (t, 1H), 7.04 (s, 1H), 6.96-6.91 (m, 2H), 6.88 (d, 1H), 6.72 (d, 1H), 6.62 (d, 1H), 6.27-6.20 (m, 1H), 2.34 (s, 3H), 2.15 (s, 3H), 2.06 (s, 3H), 1.73 (d, 3H).
MS (+ESI) m/z 550 (MH+)

Example 11

4,5-Bis-(3,4-dichloro-phenyl)-2-(1-phenyl-ethyl)-2H-pyridazin-3-one (11)

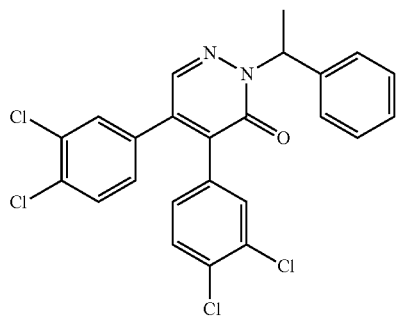 [SMILES: CC(c1ccccc1)n1ncc(-c2ccc(Cl)c(Cl)c2)c(-c2ccc(Cl)c(Cl)c2)c1=O]

Compound 11 is prepared from intermediate 1a and 3,4-dichlorophenylboronic acid under the conditions described for example 1 using tetrakis(triphenylphosphine)palladium (0), $K_2CO_3$ and a mixture of dioxane/water: 7/3. Compound 12 is isolated in solid form (yield: 54%).

F=92° C.

TLC silica gel 60 F 254 Merck, Petroleum ether-AcOEt: 80-20, Rf=0.54.

NMR $^1$H (DMSO) ppm: 8.19 (s, 1H), 7.64 (d, 1H), 7.61-7.57 (m, 2H), 7.54 (d, 1H), 7.44-7.26 (m, 5H), 7.13 (dd, 1H), 7.07 (dd, 1H), 6.30-6.22 (m, 1H), 1.75 (d, 3H)

MS (+ESI) m/z 491 (MH+)

C) Pharmacological Assessment

The pharmacological assessment of the compounds on the Kv1.5 potassium channel was performed in a 96-well plate in FLIPR technology by thallium ion measurement.

The HEK293 cells, stably transfected with the human isoform of the Kv1.5 channels, are seeded 24 h before experimentation in 96-well plates (15 $10^6$ cells/plate, 200 µl/well) polylysinated in the following culture medium: DMEM, 10% SVF, Penicillin/Streptomycin, G418 as the selection antibiotic.

The experimentation in FLIPR is performed using the "FLIPR Potassium Ion Channel Assay Kit) as indicated by the manufacturer (Molecular Devices).

Briefly, the culture medium is replaced by the solution containing the thallium marker for 90 min at 37° C. Following this step, the compounds to be tested are added to a final concentration of 10 µM in the well for 15 min at 37° C. The basic fluorescence is subsequently read for 60 secs. The addition of a depolarising medium (20 mM of potassium and 3 mM of final thallium), opens the potassium channels and induces an increase in the fluorescence of the fluorophore thallium corresponding to an influx of thallium ions through the hKv1.5 channels. The measurement is performed 30 secs after injection of the depolarising solution. Application of 10 µM of DPO (Tocris, Kv1.5 channel blocker) allows normalisation of the fluorescence.

TABLE 1

| Examples | % inhibition at 10 µM |
| --- | --- |
| BMS394136 | 99.6 |
| 1 | 100 |
| 2 | 100 |
| 3 | 43.3 |
| 4 | 54.9 |

TABLE 1-continued

| Examples | % inhibition at 10 µM |
| --- | --- |
| 5 | 93.6 |
| 6 | 94.2 |
| 7 | 54.9 |
| 8 | 88 |
| 9 | 60.1 |

*BMS394136 is a Kv1.5 channel blocker under development at Bristol - Myers Squibb (Abstract, D. Xing et al. Circulation 2009, 120 (18S3): 2515).

The results obtained show that the compounds of general formula (I) block the Kv1.5 channel.

The compounds of general formula (I) may be used as Kv1.5 channel blockers.

D) Abbreviations

TLC Thin Layer Chromatography
DMF Dimethylformamide
DMSO Dimethylsulfoxide
DPO (2-isopropyl-5-methyl-cyclohexyl) diphenylphosphine oxide
HPLC High Performance Liquid Chromatography
Rf Reference front
NMR Nuclear magnetic resonance
THF Tetrahydrofuran

The invention claimed is:

1. Compounds of formula I:

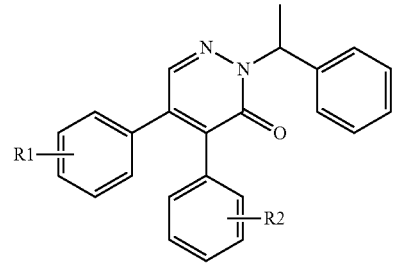

wherein $R_1$ and $R_2$ simultaneously or independently represent one or two groups chosen from: halogen, linear or branched $C_1$-$C_4$ alkyl, hydroxyl, linear or branched $C_1$-$C_4$ alkoxy, nitrile or arylsulfonamido the aryl of which is optionally substituted b a linear or branched $C_1$-$C_4$ alkyl group, as well as the different enantiomers and their mixtures in all proportions, and their pharmaceutically acceptable salts.

2. Compounds of formula I according to claim 1 wherein

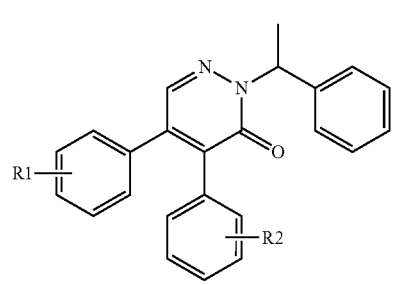

$R_1$ represents a hydroxy, methoxy or cyano group;
$R_2$ represents one or two groups chosen from: halogen such as F, Br, Cl, linear or branched $C_1$-$C_4$ alkyl, hydroxy, linear or branched $C_1$-$C_4$ alkoxy, nitrile;

as well as the different enantiomers and their mixtures in all proportions, and their pharmaceutically acceptable salts.

3. Compounds of general formula I according to claim 1 or 2 wherein:

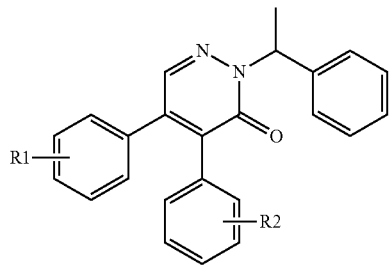

I

R$_1$ represents a hydroxy group;
R$_2$ represents one or two groups chosen from: halogen such as F, Cl, linear or branched C$_1$-C$_4$ alkyl, hydroxy, linear or branched C$_1$-C$_4$ alkoxy, nitrile;
as well as the different enantiomers and their mixtures in all proportions, and their pharmaceutically acceptable salts.

4. Compounds of general formula I according to claim 1 wherein:

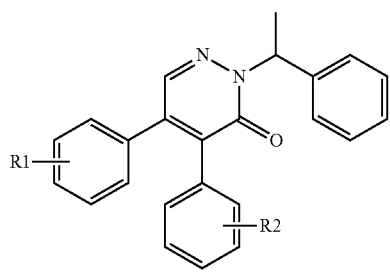

I

R$_1$ represents a hydroxy group located in para position (position 4) on the phenyl which it substitutes;
R$_2$ represents one or two groups chosen from: CL, methyl, hydroxy, methoxy, nitrile;
as well as the different enantiomers and their mixtures in all proportions and their pharmaceutically acceptable salts.

5. Compounds of general formula I according to claim 1 wherein they are chosen from: 4,5-Bis-(4-hydroxy-phenyl)-2-(1-phenyl-ethyl)-2H-pyridazin-3-one,
  4,5-Bis-(4-hydroxy-phenyl)-2-((S)-1-phenyl-ethyl)-2H-pyridazin-3-one
  4,5-Bis-(4-hydroxy-phenyl)-2-((R)-1-phenyl-ethyl)-2H-pyridazin-3-one,
  2,2,'-(6-oxo-1-(1-phenyl-ethyl)-1,6-dihydropyridazine-4,5-diyl)dibenzonitrile,
  3,3'-(6-oxo-1-(1-phenyl-ethyl)-1,6-dihydropyridazine-4,5-diyl) dibenzonitrile
  4,5-Bis-(4-methoxy-phenyl)-2-(1-phenyl-ethyl)-2H-pyridazin-3-one,
  N,N'-(3,3'-(6-oxo-1-(1-phenylethyl)-1,6-dihydropyridazine-4,5-diyl)bis(3, phenylene))bis(4-methylbenzenesulfonamide),
  3-(5-(4-methoxyphenyl)-6-oxo-1-(1-phenylethyl-ethyl)-1,6-dihydropyridazin-4-yl) benzonitrile,
  2-[5-(4-Methoxy-phenyl)-6-oxo-1-(1-phenyl-ethyl)-1,6-dihydro-pyridazin-4-yl]-benzonitrile,
  N-{3-[5-(3,4-Dimethyl-phenyl)-6-oxo-1-(1-phenyl-ethyl)-1,6-dihydro- pyridazin-4-yl]-phenyl}-4-methyl-benzenesulfonamide, or
  4,5-Bis-(3,4-dichloro-phenyl)-2-(1-phenyl-ethyl)-2H-pyridazin-3-on.

6. Process for preparation of a chemical compounds of formula 1 according to claim 1 wherein a dibromo or dichloro pyridazinone of formula 11 is condensed,

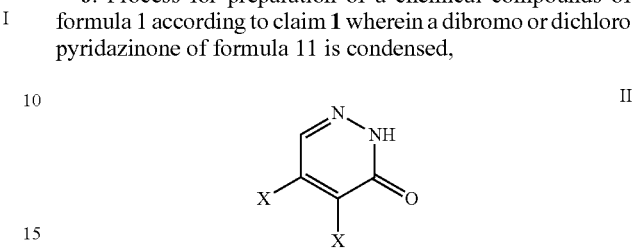

II for which X represents either a chlorine atom or a bromine atom,
with a derivative of formula III,

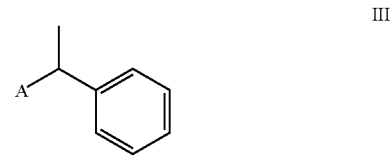

III for which:
when A represents a halogen atom, a base is used in a solvent
when A represents OH, Mitsunobu coupling conditions are used; the intermediate IV obtained

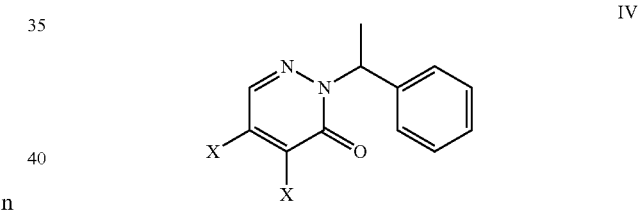

IV is subsequently coupled (step 1) with a boron derivative V

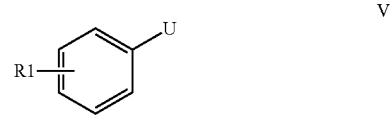

V for Which R1 as defined in claim 1 and U represents

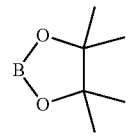

B(OH)$_2$ or
in a mixture of solvents selected from the group consisting of toluene/ethanol or water/acetonitrile or dioxane/water, in the presence of a base and a palladium catalyst;
and wherein compound VI is obtained as a major compound and compound VII is obtained as a minor compound;

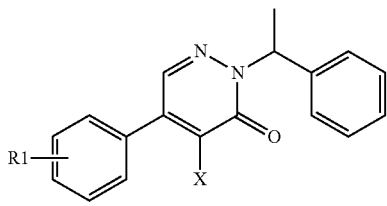

VI the intermediate VI being subsequently reacted again:
either with the boron derivative V in the coupling conditions previously described in order to yield the compound VII

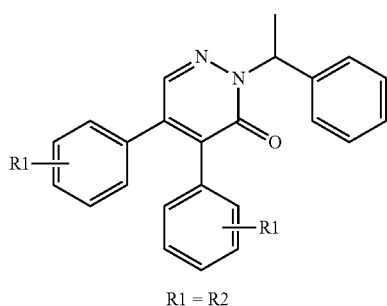

VII

R1 = R2 or with the boron derivative VIII

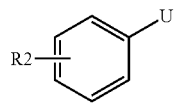

VIII for which $R_2$, is as defined in claim 1 and U is as defined above in e coupling conditions previously described for step 1 in order to yield the compound IX

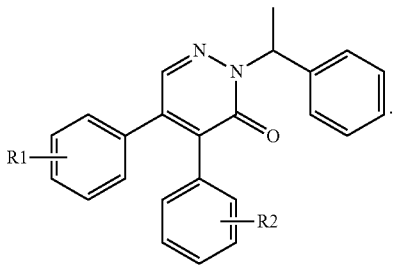

IX

R1 is different from R2

7. Method of treatment comprising administering to a patient in need thereof a compound according to claim 1, wherein the patient suffers from atrial fibrillation, or auricular and/or ventricular cardiac arrhythmias.

8. Method of blocking potassium channels comprising administering to a patient in need thereof a compound according to claim 1.

9. Pharmaceutical composition comprising a compound of general formula I according. to claim 1 in combination with at least one pharmaceutically acceptable excipient.

10. The method of claim 8, wherein the potassium channels are the Kv 1.5, Kv4.3 or Kv 11.1 channels.

11. The compound of claim 1 or 2, wherein the halogen is F, Cl or Br.

12. The process of claim 6, wherein, when condensation of pyridazone II with derivative III occurs under Mitsunobu conditions, said conditions include the presence of ethyl diethylazodicarboxylate and triphenylphosphinc, and the reaction is carried out in THF as the solvent.

13. The process of claim 6, wherein when A represents a halogen atom in derivative III, the base is $Cs_2CO_3$ and the solvent is DMF in the condensation reaction with pyridazone II.

14. The process of claim 6, wherein, in the coupling of intermediate IV with boron derivative V, the base is sodium carbonate or potassium carbonate, and the catalyst is tetrakis (triphenylphosphine)palladium or $PdCl_2/2PPh_3$.

* * * * *

UNITED STATES PATENT AND TRADEMARK OFFICE
CERTIFICATE OF CORRECTION

PATENT NO. : 8,993,569 B2
APPLICATION NO. : 13/823671
DATED : March 31, 2015
INVENTOR(S) : Elisabeth Dupont-Passelaigue et al.

Page 1 of 1

It is certified that error appears in the above-identified patent and that said Letters Patent is hereby corrected as shown below:

IN THE SPECIFICATION:

Column 7, at lines 20-25, change "  " to --B(OH)₂ or 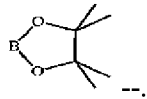 --.

IN THE CLAIMS:

In claim 1, at column 18, line 44, change "hydroxyl" to --hydroxy--.

In claim 1, at column 18, line 46, change "substituted b a" to --substituted by a--.

In claim 4, at column 19, line 44, change "CL" to --Cl--.

In claim 5, at column 19, lines 61-63, change "N,N'-(3,3'-(6-oxo-1-(1-phenyl-ethyl)-1,6-dihydropyridazine-4,5-diyl)bis(3, phenylene))bis(4-methylbenzenesulfonamide)," to --N,N'-(3,3'-(6-oxo-1-(1-phenyl-ethyl)-1,6-dihydropyridazine-4,5-diyl)bis(3, 1-phenylene))bis(4-methylbenzenesulfonamide),--.

In claim 5, at column 20, lines 4-5, change "4,5-Bis-(3,4-dichloro-phenyl)-2-(1-phenyl-ethyl)-2H-pyridazin-3-on" to --4,5-Bis-(3,4-dichloro-phenyl)-2-(1-phenyl-ethyl)-2H-pyridazin-3-one--.

In claim 6, at column 20, line 8, change "formula 11" to --formula II--.

In claim 6, at column 20, lines 55-61, change " B(OH)₂ or 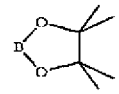 " to --B(OH)₂ or  --.

In claim 6, at column 21, line 42, change "above in e coupling" to --above in the coupling--.

Signed and Sealed this
Fifteenth Day of March, 2016

Michelle K. Lee
*Director of the United States Patent and Trademark Office*